(12) United States Patent
De Lamotte

(10) Patent No.: US 7,138,051 B2
(45) Date of Patent: Nov. 21, 2006

(54) CHROMATOGRAPHY SYSTEM, METHOD AND SOFTWARE FOR THE SEPARATION OF BIOMOLECULES

(75) Inventor: Frédéric De Lamotte, Montpellier Cedex (FR)

(73) Assignee: GE Healthcare Bio-Sciences AB, Uppsala (SE)

( * ) Notice: Subject to any disclaimer, the term of this patent is extended or adjusted under 35 U.S.C. 154(b) by 107 days.

(21) Appl. No.: 10/964,280

(22) Filed: Oct. 13, 2004

(65) Prior Publication Data

US 2005/0082228 A1    Apr. 21, 2005

Related U.S. Application Data

(60) Provisional application No. 60/543,961, filed on Feb. 12, 2004, provisional application No. 60/512,485, filed on Oct. 17, 2003.

(51) Int. Cl.
*B01D 15/08* (2006.01)

(52) U.S. Cl. .................. 210/198.2; 210/656; 210/101; 210/143

(58) Field of Classification Search ................ 210/635, 210/656, 659, 101, 143, 198.2; 95/82; 96/101
See application file for complete search history.

(56) References Cited

U.S. PATENT DOCUMENTS

| | | | | |
|---|---|---|---|---|
| 4,112,743 A | * | 9/1978 | Mowery, Jr. ................ 73/61.56 |
| 4,311,586 A | * | 1/1982 | Baldwin et al. ............ 210/101 |
| 4,767,279 A | * | 8/1988 | Dourdeville et al. .......... 417/18 |
| 5,089,124 A | * | 2/1992 | Mahar et al. ............ 210/198.2 |
| 5,112,949 A | * | 5/1992 | Vukovich .................... 530/380 |
| 5,158,675 A | * | 10/1992 | Allington et al. ........ 210/198.2 |
| 5,234,587 A | * | 8/1993 | Allington et al. ........ 210/198.2 |
| 5,670,054 A | * | 9/1997 | Kibbey et al. .............. 210/656 |
| 6,221,250 B1 | * | 4/2001 | Stafstrom .................... 210/656 |
| 6,558,551 B1 | * | 5/2003 | Anderson et al. ........... 210/660 |
| 6,652,745 B1 | * | 11/2003 | Gjerde et al. ............ 210/198.2 |
| 6,743,356 B1 | * | 6/2004 | Fermier et al. .......... 210/198.2 |
| 2001/0042714 A1 | * | 11/2001 | Gjede et al. ................ 210/634 |
| 2002/0153312 A1 | * | 10/2002 | Gjerde et al. .............. 210/635 |
| 2005/0224403 A1 | * | 10/2005 | Allington et al. ........ 210/198.2 |

* cited by examiner

*Primary Examiner*—Ernest G. Therkorn
(74) *Attorney, Agent, or Firm*—Dwayne L. Bentley; Yonngang Ji

(57) ABSTRACT

The present invention relates to methods, systems and software for optimising the separation of a sample of biomolecules eluted from a chromatography column in which the concentration of a second component added to an elution buffer is varied in order to form an elution buffer solution of varying second component concentration. The concentration of the elution buffer solution is held at a current value when a hold gradient event occurs and the the varying of the concentration of the elution buffer solution is restarted when a restart gradient event occurs. A hold gradient event occurs when a detector signal relating to the amount of biomolecules in the elution buffer solution rises past a first threshold and a restart gradient event occurs when the signal falls past a second threshold.

6 Claims, 7 Drawing Sheets

CHROMATOGRAPHY SYSTEM, METHOD AND SOFTWARE FOR THE SEPARATION OF BIOMOLECULES

REFERENCE TO RELATED APPLICATIONS

This application claims the benefit of U.S. Provisional Application Nos. 60/512,485, filed Oct. 17, 2003 and 60/543,961, filed Feb. 12, 2004.

FIELD OF THE INVENTION

The present invention relates to chromatography methods, systems and software for the separation of biomolecules.

BACKGROUND OF THE INVENTION

Retentive chromatographic separations are chromatographic methods where biomolecules in a sample are retained on a chromatography resin and are subsequently eluted. Retentive separations can use either batch adsorption techniques, i.e., where the absorption takes place in a slurry with the chromatography resin, or by column absorption techniques, i.e., where the adsorption takes place by running a solution containing the biomolecules through a column. In either case of retentive chromatographic separation, the biomolecules can be bound to the column resin, e.g., by an ionic, hydrophobic, or affinity interaction.

Following binding of the biomolecules to the chromatography resin, the biomolecules are eluted from the column. Certain methods of elution allow the skilled artisan to specifically control the point in the elution that the biomolecules of interest are released from the resin. These methods include, but are not limited to, use of a salt gradient, gradually mixing an aqueous buffer with an organic solvent, or the gradual addition of detergents. Based on the conditions used, a biomolecule may elute from a column very sharply, i.e., in a small number of fractions, or it may elute more broadly, i.e., in a larger number of fractions. It is often possible for the skilled artisan to adjust the elution conditions to optimise the separation of biomolecules of interest from unwanted material during elution, and to sharpen the peak at which a biomolecule elutes. This is referred to as improving the resolution of the chromatography process.

The standard method of assessing the resolution of a chromatographic separation is for a skilled operator to monitor the elution profile with a UV detector for absorbance at 280 mm, which provides a rough measurement of total protein eluting in a given fraction. In the case that an operator is eluting a column by means of, for example, a buffer solution of gradually changing salt gradient, if the UV detector shows an increase in the amount of protein in the eluate discharged from the column then the operator could arrange for this fraction of the eluate to start to be collected in a reservoir in a fraction collector.

The collection of the fraction would continue until the amount of protein detected in the eluate dropped below a threshold value at which point the eluate discharged from the column could be collected in a different reservoir in the fraction collector or discharged to waste. As it is very wasteful to have a trained operator continuously monitoring a chromatography run then it is usual to perform the analysis of a sample in two (or more) runs.

In the first run the sample is separated in a column while using a user chosen gradient which it is hoped will produce a satisfactory separation. The resulting chromatogram is then analysed be the operator who then defines a new, optimised gradient which is expected to give a better separation. The optimised gradient may have a different starting point and/or end point and/or slope and/or number of steps. The purpose of the optimisation is to modify the separation of the sample so that the peak(s) containing the biomolecule(s) of interest is(are) far away from the peaks containing contaminants. The sample is then separated in a second, optimised run using the newly defined gradient. If the separation is still not satisfactory then the user may redefine the optimised gradient and perform a further run or runs.

An automated system for performing a separation using a gradient is described in U.S. Pat. No. 5,112,949. A problem with such manual and automated systems with gradually changing gradients is that if the gradient is made shallow then it takes a lot of time to perform the elution and if the gradient is made steep then instead of each biomolecule of interest being eluted in turn the elution of the biomolecules overlap. This leads to several species of biomolecules being collected in each fraction instead of each specie of biomolecule being collected in its own, separate fraction.

SUMMARY OF THE INVENTION

According to the present invention, at least some of the problems with the prior art are solved by means of a chromatography system having the features present in the characterising part of claim 1 and a method having the features mentioned in the characterising part of claim 7, of U.S. Patent Publication No. 2005/0082228. Software for performing a method in accordance with the present invention has the features mentioned in claim 8, of U.S. Patent Publication No. 2005/0082228.

BRIEF DESCRIPTION OF THE FIGURES

FIG. 2b shows the results of an elution using a first embodiment of a method in accordance with the present invention using the same sample as used in the method of FIG. 2a;

FIG. 3b shows the detector signal for an elution using a first embodiment of a method in accordance with the present invention using the same sample as used in the method of FIG. 3a;

FIG. 3c shows the detector signal for an elution using a second embodiment of a method in accordance with the present invention using the same sample as used in the method of FIG. 3a;

DETAILED DESCRIPTION OF THE PREFERRED EMBODIMENTS

Figure 1:
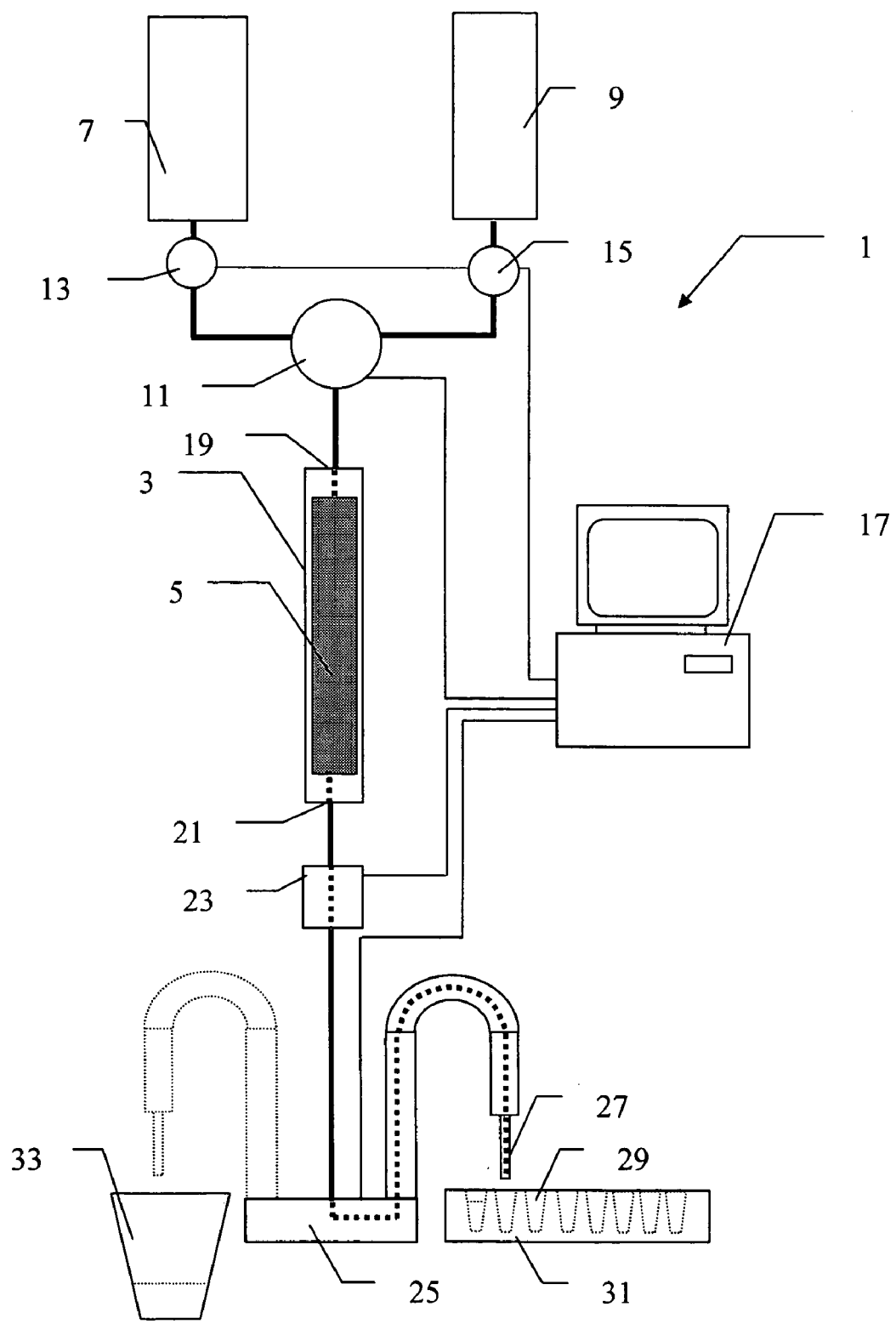
FIG. 1 shows schematically a first embodiment of a chromatography device in accordance with the present invention.

FIG. 1 shows schematically a first embodiment of an automated chromatography system 1 in accordance with the present invention for the elution of biomolecules. System 1 comprises a chromatography column 3 which contains a separation medium 5, for example, but not limited to, an ion exchange medium, a hydrophobic interaction medium, an affinity medium or a reverse phase HPLC medium, onto which the biomolecules of interest have been bound. In order to release the biomolecules from the medium 5 it is necessary to elute the column 3 with a buffer gradient, for example by providing a flow of a buffer solution which contains an increasing concentration of a second component, e.g. salt, through the column.

Such a second component (e.g. salt) gradient can be achieved by providing a buffer reservoir 7 containing buffer and a concentrated second component (e.g. salt) solution reservoir 9 containing a second component (e.g. concentrated salt solution), which reservoirs 7, 9 are connectable to mixing valve 11 in which the buffer and concentrated second component solutions can be mixed together in gradually varying proportions to produce an elution buffer of gradually varying second component concentration. This elution buffer is able to break the bonds binding biomolecules to the chromatography medium, with different bonds being broken at different second component concentrations.

Pumps 13, 15 are provided to move the buffer solution and second component solution from the respective reservoirs 7, 9 to the mixing valve 11 and to the column 3. A control means such as computer 17 provided with control software is operatively connectable to the mixing valve 11 and pumps 13, 15 in order to control the concentration and flow rate of the elution buffer. The elution buffer is inputted to a first end 19 of the column 3 and is outputted from the second end 21 of the column.

The outputted elution buffer passes a UV-detector 23 arranged to measure the strength of a beam of UV-light after it has passed through the elution buffer. The UV-detector 23 produces a detection signal which varies in dependence on the amount of UV-light absorbing material in the elution buffer and this signal is transmitted to control means 17. After passing the UV-detector 23 the elution buffer passes through a fraction collector 25. Fraction collector 25 comprises a movable outlet pipe 27 which under the control of the control means 17 can be moved to positions above fraction collecting reservoirs, e.g. wells 29 in a micro-titre plate 31 or to a waste collector, e.g. waste reservoir 33, for later disposal, or a waste drain (not shown).

The software in control means 17 may be provided with factory set or, preferably, user settable fraction collecting start and stop UV-transmission thresholds for determining which fractions of elution buffer passing the UV-detector are collected into fraction collecting reservoirs and which fractions are sent to the waste collector or drain. For example, the fraction collecting start UV-threshold may be set at 10%, i.e. a 10% drop from the maximum level of UV light detected (when the maximum level corresponds to elution buffer containing no biomolecules and increasingly lower levels correspond to increasing amounts of biomolecules in the eluted elution buffer) after it has passed through the eluted elution buffer could cause the elution buffer to be start to be collected in a fraction collection reservoir. The fraction collecting stop threshold could be set at, for example, 5%, —this would mean the fraction collecting will continue until the level of UV light detected after it has passed through the eluted elution buffer has returned to 95% of the maximum level—at this point the eluted elution buffer could be sent to waste or to a different fraction collection reservoir.

The software is further provided with a gradient controlling routine. In a first embodiment of the present invention, the gradient controlling routine is adapted to cause control device 17 to operate pumps 13, 15 and mixing valve 11 to provide an increasing salt concentration gradient which increases at a constant rate until a "hold gradient event" occurs. In this embodiment, a hold gradient event is a reduction in the level of UV light detected by the UV-detector 23 to a predetermined level Bmin1 corresponding to a predetermined minimum level of biomolecules in the eluted elution buffer in the UV-detector 23. This corresponds to the start of a specific biomolecule being eluted from the column medium. Once a hold gradient event occurs the gradient is placed on hold, i.e. the pumps 13, 15 and mixing valve 11 are operated so that the salt concentration is maintained at its current level, and this concentration is maintained until a "restart gradient event" occurs. Preferably, while the salt concentration is maintained at this level the eluted elution buffer and the specific biomolecules are collected in a new fraction collection reservoir 29.

A restart gradient event is an increase in the level of UV light detected to the level Bmin1 (or, alternatively, a second user-defined restart threshold Bmin2) corresponding to the amount of biomolecules in the eluted elution buffer in the UV-detector 23 falling below that of the predetermined minimum level of biomolecules in the eluted elution buffer—this corresponds to the end of the elution of the specific biomolecule. Once a restart gradient event has occurred the gradient controlling routine causes the pumps 13, 15 and mixing valve 11 to restart increasing at a constant rate the concentration of the elution buffer.

This continues until the next hold gradient event occurs at which time the gradient is again put on hold, and the new specific biomolecule collected in a new fraction collection reservoir 29, until a gradient restart event occurs and so on. In this embodiment, by preventing increases in the concentration gradient once the amount of a biomolecule in the eluted elution buffer has reached a predetermined level and maintaining the concentration level constant until the amount of biomolecule has fallen below a predetermined concentration level, the risk that the elution of several biomolecules will overlap is reduced.

Figure 2A:
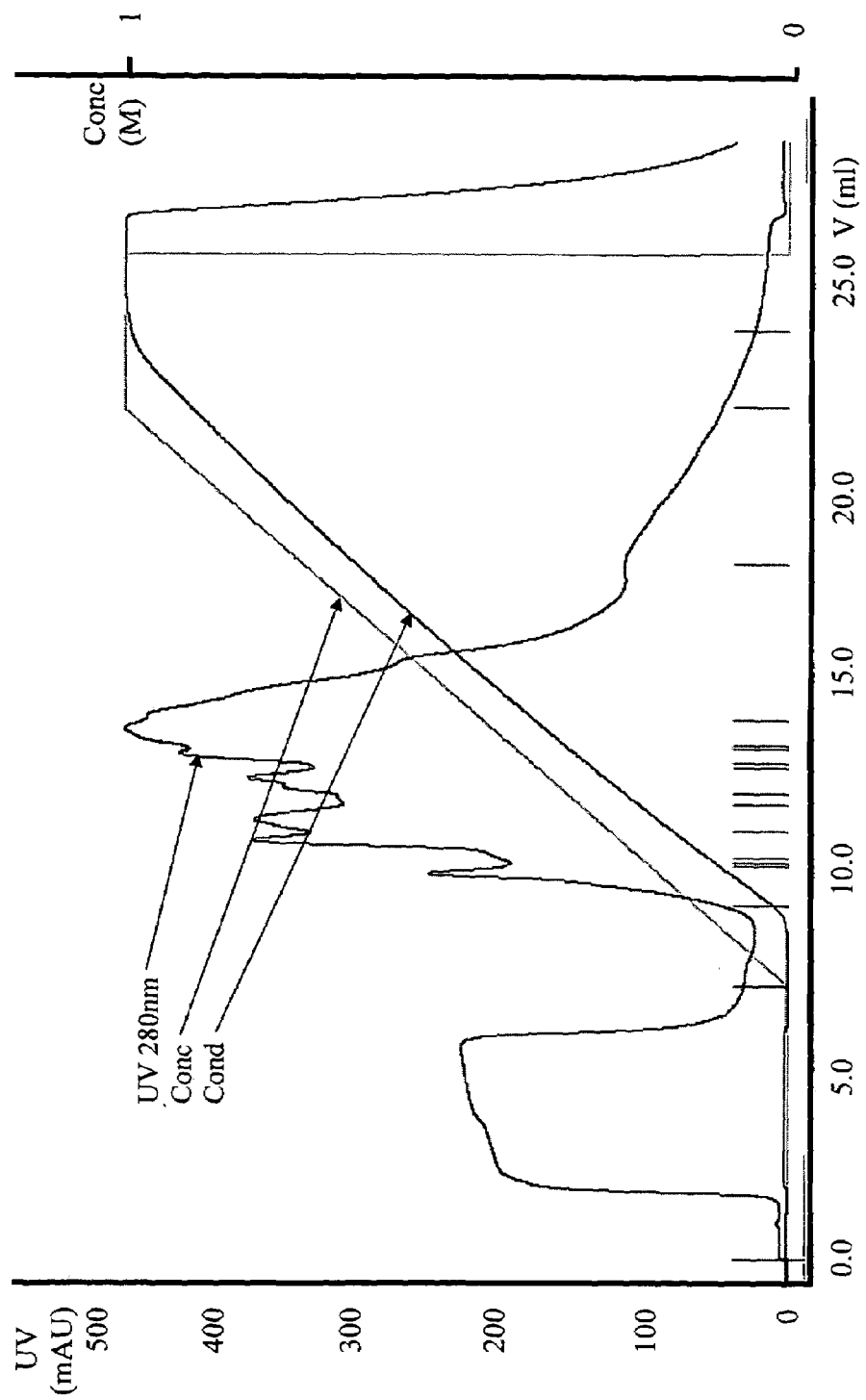
FIG. 2a shows the results of elution of a sample containing biomolecules in accordance with a prior art elution method.
Figure 2B:
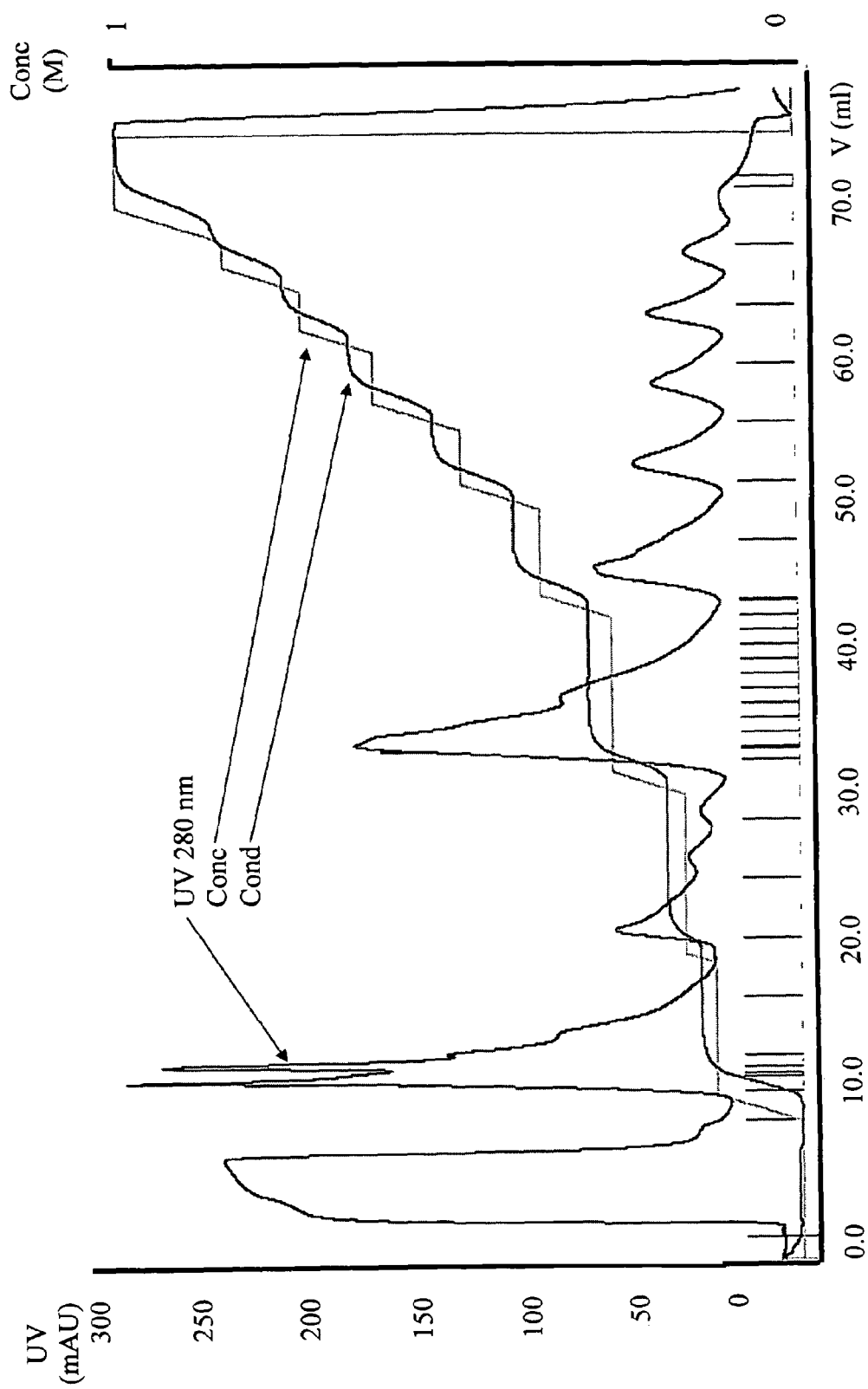

This can be seen by a comparison of FIGS. 2a and 2b. FIGS. 2a and 2b show the results of separations of a sample of crude wheat germ extract which was separated on a column containing MonoS chromatography medium (from Amersham Biosciences AB, Uppsala, Sweden) using an elution buffer solution of Sodium Acetate 40 mM, pH 4 with an increasing concentration (Conc) of NaCl (from zero to a final strength of 1M). FIG. 2a shows a prior art elution at constant concentration gradient and FIG. 2b shows the elution of the same sample using an elution method in accordance with a first embodiment of the present invention. In each figure the line UV 280 nm shows the signal from the UV-detector, the line "Conc" shows the desired NaCl concentration in the buffer and "Cond" shows the actual NaCl concentration in the buffer. In the prior art the biomolecules are eluted in a small number of indistinct, broad peaks which are collected as 17 fractions (the start of each fraction being shown as a vertical line above the X-axis), while in the method in accordance with an embodiment of the present invention the biomolecules are eluted in a larger number of more distinct, narrow peaks which can be collected in 34 fractions.

In a second embodiment of the present invention, the gradient control routine is adapted to control the flow of elution buffer as well as the salt concentration—as described above in connection with the first embodiment of the present invention. In this embodiment, when a hold gradient event occurs, the pumps are controlled to reduce the elution buffer flow rate from its original rate to a biomolecule elution rate.

This means that the speed of the flow past the UV detector is decreased and this allows small changes in the amount of eluted biomolecules to be more accurately detected and may allow better separation of molecules having similar adsorption properties for the medium being used in the column. When a restart gradient event occurs the pumps are controlled to increase the flow back to its original rate.

In a third embodiment of the present invention, the gradient control routine is adapted to control the rate of change of the gradient of the salt concentration in addition to controlling the parameters mentioned in the first or second embodiments of the present invention. In this embodiment, when a restart gradient event occurs, the pumps are controlled to increase the salt concentration at an increasing rate, i.e. to increase the slope of the salt concentration gradient. This increase in slope can be used to compensate for the extra time that the elution would otherwise require due to the salt concentration being held at a constant level between hold gradient and restart gradient events.

In a preferred embodiment of the present invention, a hold gradient event is defined by a rate of change of the signal outputted from the UV-detector exceeding a threshold rate Rmin1, for example, a change of more than 100 mAU/min in the signal from the UV-detector. Similarly, a restart gradient event is defined by the rate of change of the signal outputted from the UV-detector falling below a threshold rate Rmin2, e.g. 75 mAU/min. In this embodiment a peak in the amount of biomolecules in the eluted elution buffer will be detected more rapidly than in the previous embodiments of the present invention. Additionally, this preferred embodiment of the present invention is less sensitive to UV-detector baseline drift than the previous embodiments.

Baseline drift refers to changes in the level of detector noise which can occur during a separation. As is well known, all detectors suffer from a level of random noise and at the start of a separation the current level of noise (which is the detector signal level in the absence of any biomolecules in the buffer passing through the UV-detector) is set as the zero level for the detector. This zero level is also called a baseline. The baseline noise level is not always stable and during use baseline drift can occur, i.e. the random noise can drift to a different level which could be confused with a genuine signal indicating the presence of a biomolecule. Another cause of baseline drift is changes in the composition of the elution buffer solution—for example if the UV absorbtion of the second buffer component is greater than that of the buffer then as the concentration of the second component increases the baseline will also increase.

The effects of baseline drift can be illustrated by considering the case when the baseline drift in the UV-detector system is so much that the level of noise changes from its original zero level to a level which is the same as, or greater than, the signal level Bmin1. In the previous embodiments of the present invention, as soon as the noise level exceeds Bmin1, the routine will determine that this is a hold gradient event and the routine will cause the gradient to be held at a constant value. As long as the noise persists above the restart gradient event threshold Bmin1, alternatively Bmin2, the routine will maintain the gradient at the constant value. This is undesirable as it will prolong the elution unnecessarily.

In the preferred embodiment of the present invention, noise in the UV-detector system will only generate a hold gradient event if the level of noise changes at a rate greater than rate Rmin1. It will not generate a hold gradient event if the noise level passes a certain valve except in the case that the rate in increase of the noise is equal to, or exceeds, the rate Rmin1. If noise increases at a rate equal to or greater than rate Rmin1 then the routine will hold the gradient at the current value—however normally it is not possible for noise to sustain a rate of change over Rmin1 for long and as soon as it falls below Rmin1, alternatively Rmin2, the routine will consider that a restart gradient event has occurred and it will start increasing the gradient again. Consequently, a baseline drift will not be mistaken for a hold gradient event unless the rate of drift is equal to, or greater than, Rmin1.

Figure 3A:
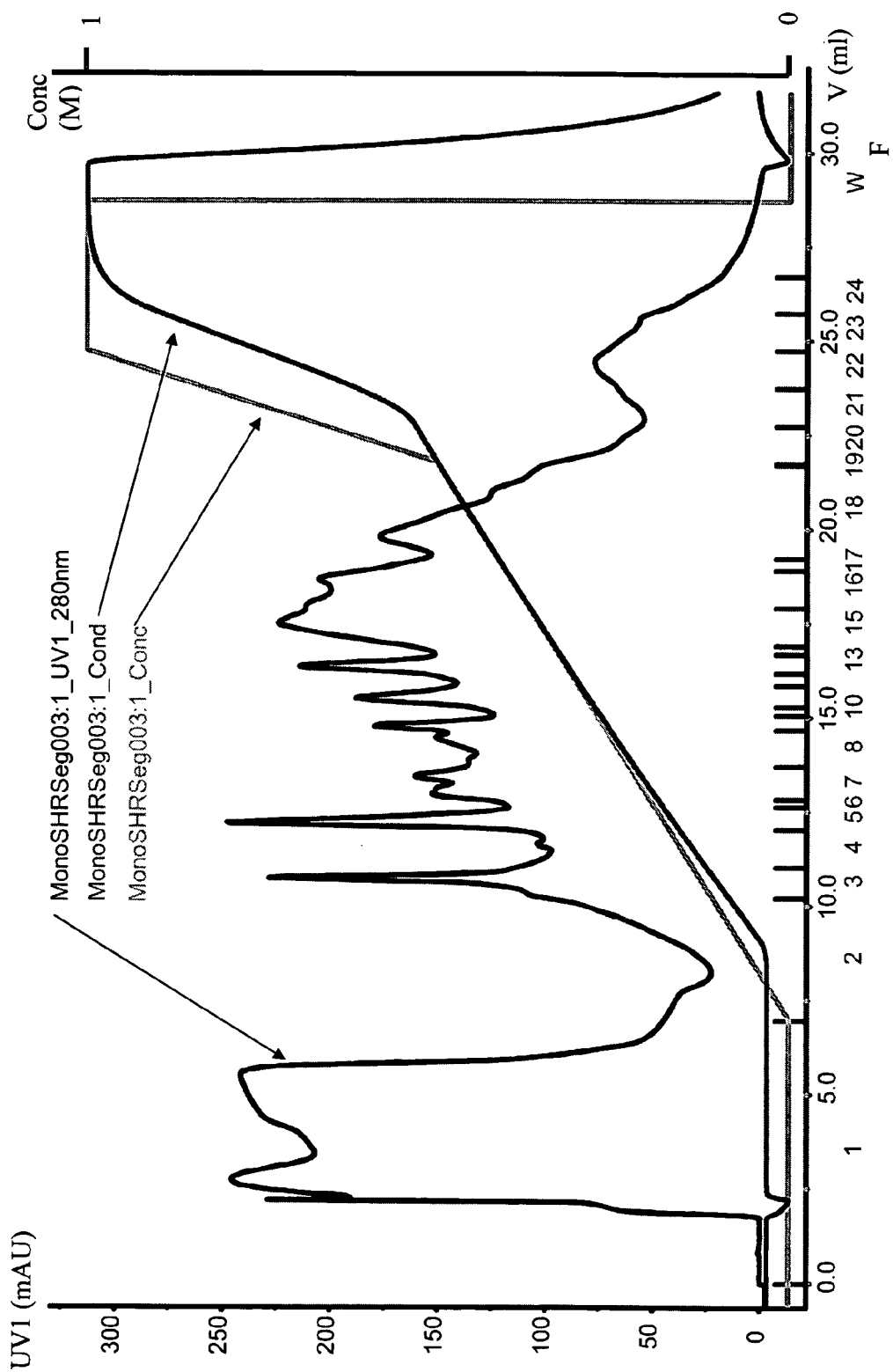
FIG. 3a shows the detector signal for the elution of another sample containing biomolecules in accordance with a prior art elution method.
Figure 3B:
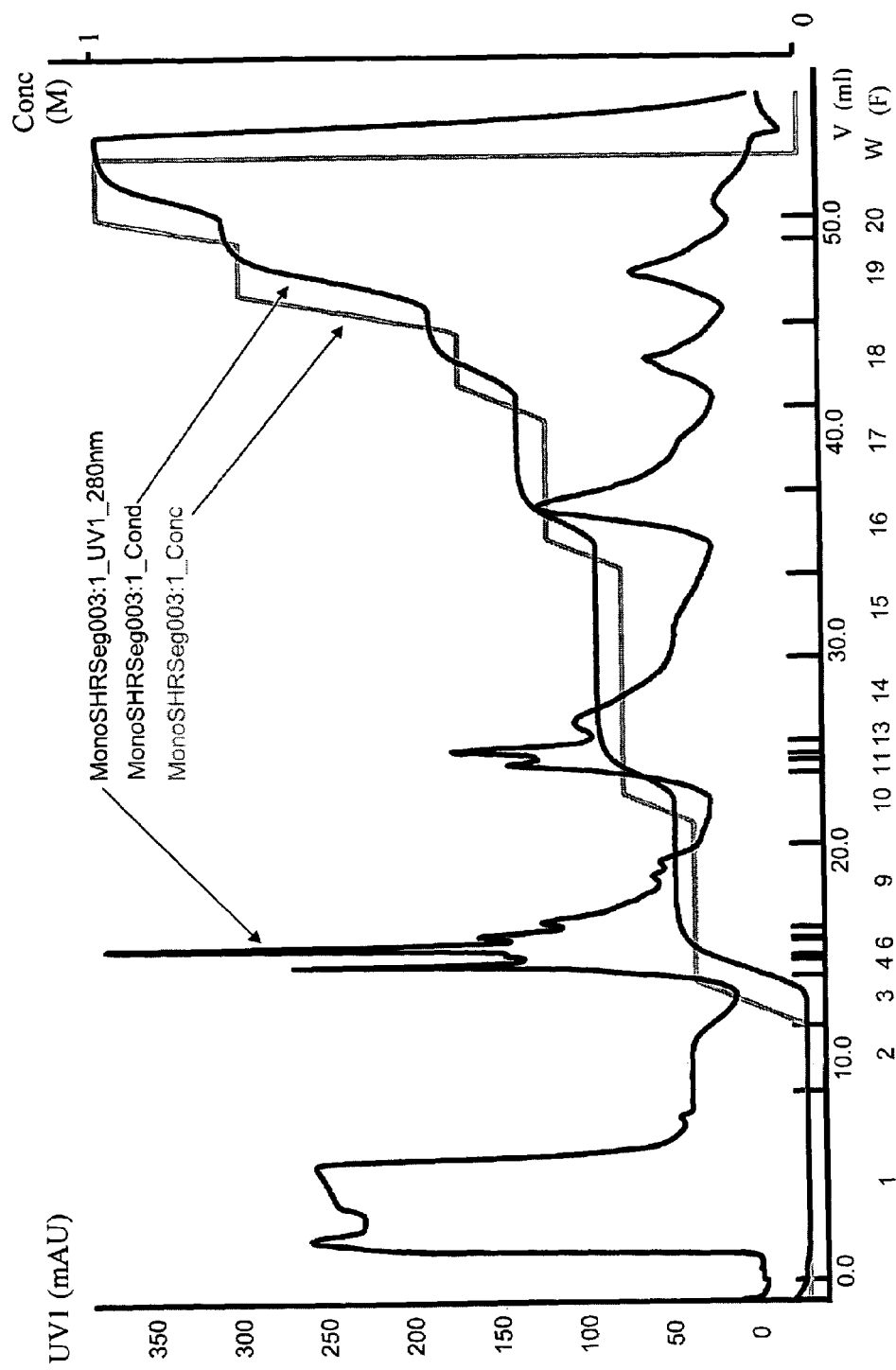
Figure 3C:
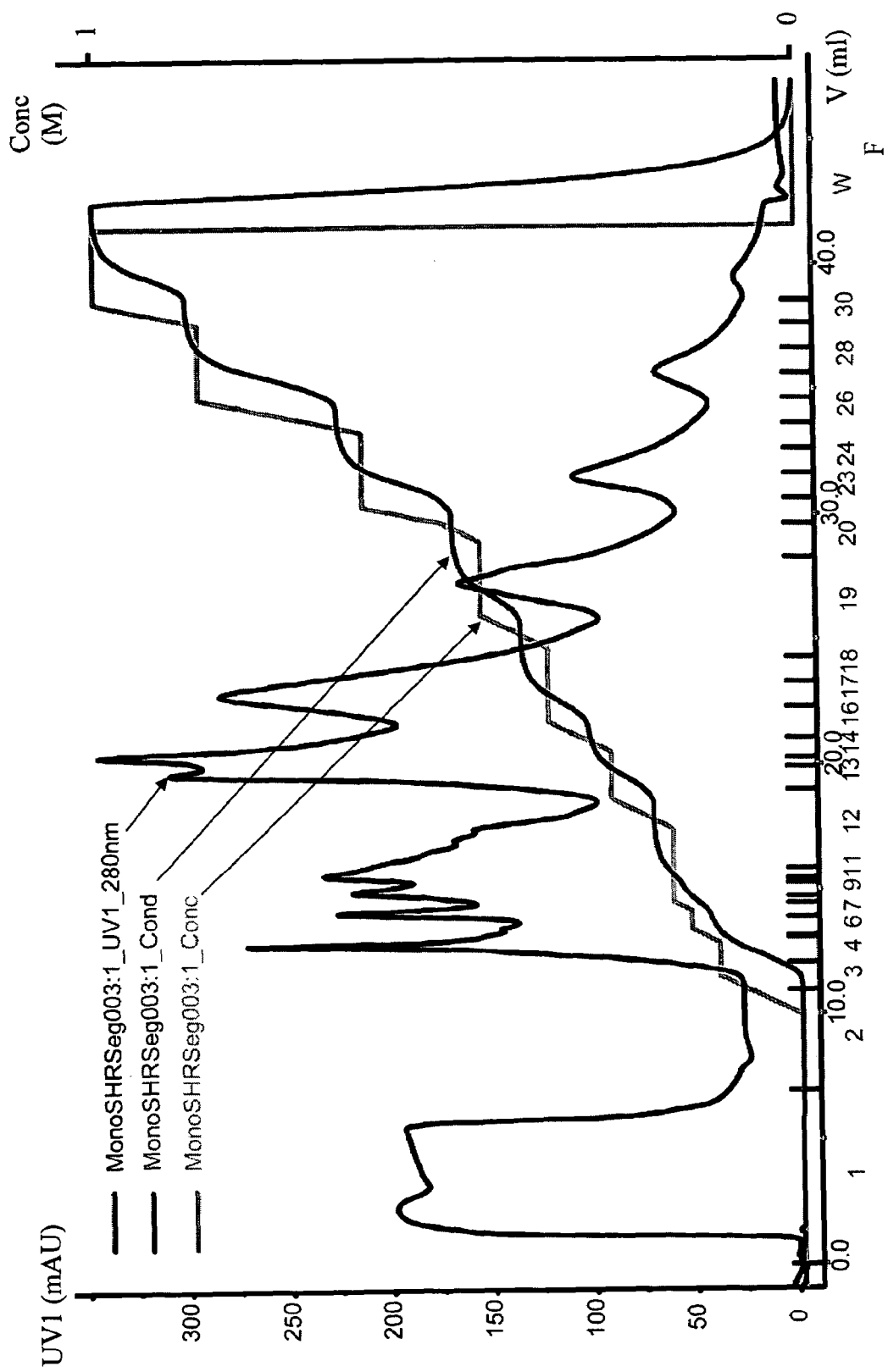

FIGS. 3a–3c show the results of separations of a sample of crude wheat germ extract which was separated on a column containing MonoS chromatography medium (from Amersham Biosciences AB, Uppsala, Sweden) using an elution buffer solution of Sodium Acetate 40 mM, pH 4 with an increasing concentration of NaCl (from zero to a final strength of 1M). FIG. 3a shows a prior art elution at constant concentration gradient. Here it is desired that the gradient rises at a first constant gradient and then a second steeper gradient as shown by the line MonoSHRSEG003:_Conc. The actual concentration gradient achieved is shown by the line MonoSHRSEG003:_Cond. The difference between the desired and actual concentrations is caused by limitations of the mixing valve and pumps. The signal corresponding to the UV light level detected by the UV-detector is shown by the line MonoSHRSEG003:_UV1_280 nm. The bottom axis of the figure shows the volume (V) of elution buffer eluted in millilitres, and the number of fractions (F) collected. "W" stands for "waste" and indicates that after the last fraction has been collected the following elution buffer is discarded. In this case, the biomolecules were eluted in a volume of 30 ml elution buffer solution and separated into 24 fractions.

FIG. 3b shows the elution of a volume of the same sample using an elution method in accordance with the present invention in which the gradient is put on hold when the UV-detector signal reaches a threshold level Bmin1. Bmin1 was set at 30 mAU and Bmin2 was set at 25 mAU. In this case, the biomolecules were eluted in a volume of 55 ml and separated into 20 fractions.

FIG. 3c shows the elution of the same sample using an elution method in accordance with an embodiment of the present invention in which the concentration gradient is put on hold when the rate of change of the UV-detector signal reaches a threshold level Rmin1. Rmin1 was set at 100 mAU/min and Rmin2 was set at −75 mAU/min. In this case the biomolecules were eluted in a volume of 42 ml and separated into 30 fractions.

Figure 4:
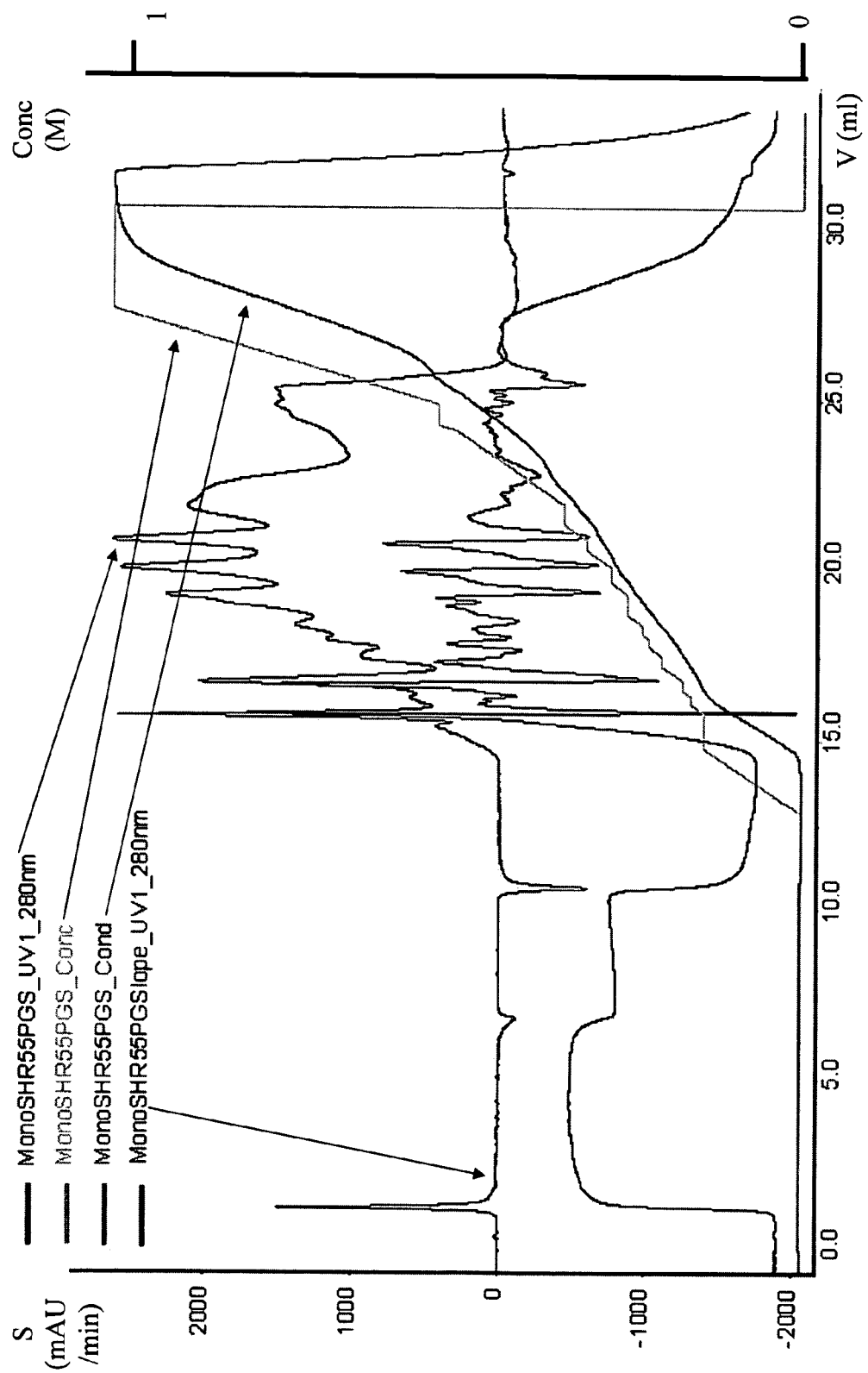
FIG. 4 shows the rate of change of a detector signal for an elution similar to that shown in FIG. 3c.

FIG. 4 shows an example of an elution similar to that of FIG. 3c where the rate of change of the UV-detector signal (S) in mAU/min, the UV-detector signal, and the desired and actual salt concentrations are shown.

In all of the embodiments of the present invention, it is possible to use the gradient control routine to also control the collection of fractions. Thus whenever a hold gradient event occurs the routine could control the fraction collector to start collecting the elution buffer solution that is leaving the column in a new fraction collecting reservoir and when a restart gradient event occurs the routine could control the fraction collector to stop collecting in the current fraction collecting reservoir the elution buffer being eluted and to send the elution buffer solution leaving the column to waste or to another fraction collecting reservoir.

One of the major advantages of systems, methods and software in accordance with the present invention is that it is possible to optimise the separation of a sample using a single chromatography run instead of the two (or more) runs previously needed.

Preferably a system in accordance with the present invention is implemented on an Akta™ chromatography system (available from Amersham Biosciences AB, Uppsala, Sweden) and the gradient control routine is provided in Unicorn™ software (also from Amersham Biosciences AB, Uppsala, Sweden).

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A chromatography system for the separation of biomolecules, comprising a chromatography column containing a medium to which biomolecules can bind and means for eluting biomolecules from the column using an elution buffer solution, said elution buffer solution having a variable concentration of a second component, wherein the concentration of said second component is controllable by a control device containing software which can cause said concentration of said second component to change at a desired gradient and wherein said control device is able to receive output signals from a detector, is able to produce output signals related to amount of biomolecules in the elution buffer solution eluted from said column, wherein changes in the concentration of said second component in said elution buffer solution are prevented when said software detects a hold gradient event and further changes in said concentration are permitted when said software detects a restart gradient event.

2. The chromatography system of claim 1, wherein a hold gradient event is considered to have occurred when said output signal from said detector is equal to or greater than a first threshold signal level (Bmin1).

3. The chromatography system of claim 2, wherein a restart gradient event is considered to have occurred when said output signal from said detector is less than a second threshold signal level (Bmin2).

4. The chromatography system of claim 3, wherein the value of the second threshold signal level Bmin2 is not the same as the value of the first threshold signal level Bmin1.

5. The chromatography system of claim 1, wherein a hold gradient event is considered to have occurred when said output signal from said detector changes at a rate which is equal to or greater than a first threshold signal level rate of change (Rmin1).

6. The chromatography system of claim 1, wherein a restart gradient event is considered to have occurred when said output signal from said detector changes at a rate which is less than a second threshold signal level rate of change (Bmin2).

* * * * *